(12) United States Patent
Han et al.

(10) Patent No.: US 8,569,714 B2
(45) Date of Patent: Oct. 29, 2013

(54) DOUBLE TILT TRANSMISSION ELECTRON MICROSCOPE SAMPLE HOLDER FOR IN-SITU MEASUREMENT OF MICROSTRUCTURES

(75) Inventors: Xiaodong Han, Beijing (CN); Yonghai Yue, Beijing (CN); Yuefei Zhang, Beijing (CN); Pan Liu, Beijing (CN); Kun Zheng, Beijing (CN); Xiaodong Wang, Beijing (CN); Ze Zhang, Beijing (CN)

(73) Assignee: Beijing University of Technology, Beijing (CN)

( * ) Notice: Subject to any disclaimer, the term of this patent is extended or adjusted under 35 U.S.C. 154(b) by 0 days.

(21) Appl. No.: 13/519,291

(22) PCT Filed: Jul. 11, 2011

(86) PCT No.: PCT/CN2011/077033
§ 371 (c)(1),
(2), (4) Date: Jun. 26, 2012

(87) PCT Pub. No.: WO2012/162929
PCT Pub. Date: Dec. 6, 2012

(65) Prior Publication Data
US 2013/0105706 A1 May 2, 2013

(51) Int. Cl.
*G01N 1/28* (2006.01)
*H01J 37/20* (2006.01)
(52) U.S. Cl.
USPC .................................. 250/440.11; 73/864.91
(58) Field of Classification Search
USPC .................... 250/440.11; 73/864.91
See application file for complete search history.

(56) References Cited

U.S. PATENT DOCUMENTS 6,967,335 B1 * 11/2005 Dyer et al. ............... 250/442.11
2002/0194938 A1 12/2002 Koo et al.
(Continued)

FOREIGN PATENT DOCUMENTS

| CN | 1662838 A | 8/2005 |
| CN | 101275895 A | 10/2008 |

(Continued)

OTHER PUBLICATIONS

J.W. Lau, M.A. Schofield, Y.Zhu; A straightforward specimen holder modification for remnant magnetic-field measurement in TEM; Oct. 4, 2006; Ultramicroscopy 107 (2007), pp. 396-400.*

(Continued)

*Primary Examiner* — Robert Kim
*Assistant Examiner* — Kevin Chung
(74) *Attorney, Agent, or Firm* — Han IP Corporation

(57) ABSTRACT

A double tilt sample holder for in-situ measuring mechanical and electrical properties of microstructures in transmission electron microscope (TEM) is provided. The sample holder includes a home-made hollow sample holder body, a sensor for measuring mechanical/electrical properties, a pressing piece, a sample holder head, a sensor carrier. The sensor for measuring mechanical/electrical properties is fixed on the sensor carrier on the sample holder head by the pressing piece, while the sensor carrier is connected to the sample holder head through a pair of supporting shafts located on sides of the sample holder head. The sensor carrier can tilt within the plane perpendicular to the ample holder head by revolving around the supporting shafts (i.e. tilting along Y axis at an angle of ±30°). The sample holder also allows obtaining mechanical/electrical parameters concurrently.

4 Claims, 4 Drawing Sheets

(56) References Cited

U.S. PATENT DOCUMENTS

| | | | |
|---|---|---|---|
| 2003/0127595 A1* | 7/2003 | Nakamura et al. | 250/311 |
| 2006/0289784 A1 | 12/2006 | Deguchi et al. | |
| 2010/0154557 A1* | 6/2010 | Han et al. | 73/800 |
| 2011/0107472 A1* | 5/2011 | Han et al. | 850/53 |

FOREIGN PATENT DOCUMENTS

| | | |
|---|---|---|
| CN | 102027562 A | 4/2011 |
| CN | 202134501 U | 2/2012 |
| JP | 2002319365 A | 10/2002 |
| JP | 2008262921 A | 10/2008 |

OTHER PUBLICATIONS

Analytical Holders Single Tilt/Double Tilt Analytical Holders for TEM; Apr. 1, 1996; Gatan Inc.*

* cited by examiner

DOUBLE TILT TRANSMISSION ELECTRON MICROSCOPE SAMPLE HOLDER FOR IN-SITU MEASUREMENT OF MICROSTRUCTURES

CROSS-REFERENCE TO RELATED APPLICATION

This application is the national phase application of International application number PCT/CN2011/077033, filed Jul. 11, 2011, which claims the priority benefit of Chinese Patent Application No. 201110145305.8, filed on May 31, 2011, which is hereby incorporated by reference in its entirety.

TECHNICAL FIELD

The present disclosure relates to a sample holder for a transmission electron microscope (TEM) for measuring various properties of the sample. The sample holder tilts at a large angle around a pair of quadrature axes while simultaneously applying stress on the plane where the sample is located to realize in-situ dynamic real-time study on the microdomain deformation of materials at atomic scale. The present disclosure belongs to the technical field of in-situ measurement of TEM accessories and nanomaterials.

BACKGROUND

Since the invention of the transmission electron microscope (TEM) in 1930s (1932), especially for the past 20 years, significant progress has been made in TEM technology. With newly developed resolution enhancement technologies, such as spherical aberration (Cs) correctors for spatial resolution, monochromators for energy resolution, and high-speed CCD camera for time resolution, the modern TEM can be used to characterize a structure down to atomic scale, thus making great contributions to scientific progress in physics, chemistry, biology, materials science, and electronic information technology, etc. Meanwhile, as a current trend in TEM development, in-situ outfield measurement has been attracted increasing attention since it provides physical images for in-depth scientific studies. Direct observation of changes in microstructures of materials at atomic level provides the basis for fundamental understanding of physics, chemistry and materials science. However, due to the limitation of the current available technologies, research on the plastic deformation behavior of materials by TEM has been focused on the static material structures. It is often difficult to draw conclusions of certain findings due to the lack of knowledge on the dynamic evolution of microstructures.

The 654 and 671 type TEM sample holders produced by Gatan Company in America are the ones able to realize in-situ tensile test of sample under single tilt condition (around X axis), thus enables the real-time observation of reversible deformation twin in pure aluminum under TEM. Nanofactory Company in Sweden has developed in-situ deformation technology in TEM to study tension, compression and bending deformation as well as plastic deformation behaviors of nanowires. The PI 95 TEM picometer indenter manufactured by PI 95 Company in America can also be applied under single tilt condition (around X axis) to in-situ probe plastic deformation of various nanomaterials in TEM.

Although these commercial deformation devices in TEM provide a convenient tool for in-situ study of changes of microstructures during the deformation process of nanomaterials, information obtained is often limited. The existing commercial TEM sample holders used in in-situ mechanical behavior study normally only allow single tilting around X axis, so the tilting around Y axis cannot be realized. In addition, although the commercially available double tilt sample holder technology has been developed recently, these sample holders can only allow the observation of the sample; it is not feasible to simultaneously apply stress within the sample plane under double tilt condition. Thus the ability for in-situ study of mechanisms on the deformation, fracture, and phase change at atomic scale is significantly limited.

In particular, the above-mentioned methods apply stress on the samples by installing a complex mechanical device on the TEM sample holder. After installation of such device, the sample holder can only be used to apply stress on the sample under single tilt condition (around X axis), thus it is impossible to perform in-situ dynamic study on deformation mechanism under high-resolution state or at atomic scale, since the study also requires the application of stress while the sample is tilted around Y axis. Therefore, it poses great challenge for researcher in correctly understanding the performance of materials.

SUMMARY

To overcome existing technical problems, the object of the present disclosure is to provide a double tilt transmission electron microscope (TEM) holder for in-situ measuring mechanical and electrical properties of microstructures. The sample holder may comprise a home-made hollow sample holder body (hereinafter referred to as "sample holder body"), a sensor for measuring mechanical/electrical properties, a pressing piece, a sample holder head, and a sensor carrier. The sensor is fixed on the sensor carrier by the pressing piece. The sensor carrier is fixed on the front end of the sample holder head by a pair of supporting shafts located on the sides of the sample holder head. The sensor carrier can tilt within the plane perpendicular to the sample holder head by revolving around the supporting shafts (i.e. tilting around Y axis at an angle of ±30°). The electrodes on the sensor are connected to the electrodes disposed on two side walls of the sample holder head through the pressing piece, and then connected to the external testing equipment through conductor wires inside the sample holder body to realize the in-plane (within sensor plane) loading of mechanical/electrical signal and real-time monitoring of feedback. Therefore, the sample holder in the present disclosure not only allows tilting sample below the low-index zone axis to make in-situ observation of the sample at atomic scale, but also enables obtaining the mechanical and electrical integrated parameters of the sample concurrently.

To achieve these goals, the present disclosure is realized by the following technical solutions:

A double tilt sample holder for in-situ measuring mechanical and electrical properties in a TEM may comprise a handle 1, a sample holder body 2, a sample holder head 3, a sensor carrier 4, a sensor 11, and a pressing piece. The sensor carrier 4 is fixed on the front end of the sample holder head 3 by a pair of supporting shafts 5 located on the sides of the sample holder head 3. The sensor carrier can tilt within the plane perpendicular to the sample holder head 3 by rotating around the supporting shafts 5 (i.e. tilting around Y axis at an angle of ±30°, as illustrated in FIG. 5). Conductor wires I 6 led into the sample holder head 3 through the sample holder body 2 from the outside of TEM are distributed in a symmetrical manner along sides of the sample holder head 3. One end of the conductor wires I 6 is connected to an electrode array I 7 distributed along the sides of the sample holder head 3, and the other end of the conductor wires I 6 is connected to the electrode interface 8. The electrode interface 8 is connected to the external equipment of TEM. The electrode array I 7 is symmetrically distributed along the sides of the sample holder head 3 with the supporting shafts 5 as the centerline. The rotation of the sensor carrier 4 is driven by a Y-axis tilting actuator 9 located at its end. The sensor carrier 4 may include a groove 10 located at a position with the supporting shafts 5 as the centerline. The groove 10 is a through hole with a peripheral supporting edge at the bottom to support a sensor 11. The thickness of the senor is configured such that after the sensor is received in the groove 10, the upper surface plane of the sensor 11 and the TEM electron beam focusing point are maintained at the same plane to allow the TEM electron beam passing through the gap on the sensor 11 and groove 10 and focusing on the sample 12.

In addition, the sensor carrier 4 may also have a through hole I 13 located at a position far from the supporting shafts 5 and close to the Y-axis tilting actuator 9. The dimension of the through hole I 13 is configured in such a way that the sensor carrier 4 will not be in contact with the pole shoe of TEM when the sample holder tilts around the Y axis and when the sample holder fully revolves around X axis, thus preventing damages to the TEM. The sensor 11 is provided with two rows of electrode array II 14 that are symmetrically distributed on each side of the sensor and at a position closer to the supporting shaft 5. A pressing piece 15 is also provided an electrode array III 16 having two rows of electrodes on both upper and lower surfaces of the pressing piece 15, respectively, and each electrode of the electrode array III 16 on the upper face is electrically connected to a respective one on the lower surface by a conductor wire. After sensor 11 is received in the groove 10 of the sensor carrier 4, the pressing piece is pressed on the sensor 11. The precise design would guarantee that each electrode of the electrode array III 16 on the lower surface of the pressing piece is electrically connected with a respective one of the electrode array II 14 on the sensor 11. After fixing the pressing piece 15 on the sensor carrier 4, each electrode of the electrode array III 16 on the upper surface of the pressing piece 15 is electrically connected with a respective one of electrode array I 7 on the sample holder head 3 by a conductor wire.

In addition, the pressing piece 15 may include a through hole II 17. The dimension of the through hole II 17 is configured such that the TEM electron beam can pass through the pressing piece and be focused on the sample 12. The sensor 11 may include electrode array II 14, a stress loading part 18, a stress testing part 19, two testing electrodes 20, and a testing sample 12. The stress loading part 18 is arranged in parallel to the stress testing part 19 and to the electrode array II 14. The stress loading part 18 and the stress testing part 19 are located between two rows of electrode array II 14. The small gap between the stress loading part 18 and stress testing part 19 is configured such that the TEM electron beam can pass through it. The first testing electrode 20 is disposed on the stress loading part 18 and the second testing electrode 20 is disposed on the stress testing part 19. The sample 12 is fixed on top of the first and second testing electrodes 20 in an overlapping manner and stretched over the gap between the stress loading part 18 and the stress testing part 19. The stress loading part 18, the stress testing part 19, and two testing electrodes 20 are all connected to the electrode array II 14. The stress loading part 18 normally is made of materials that can undergo deformation under external thermal or electric field. Under thermal or electrical field, the deformation of the stress loading part 18 would make it coming closer or moving away from the stress testing part 19, thus applying tensile or compressive force on the sample. The material includes thermal bimetal strip, piezoelectric ceramics and memory alloy. The commercially available cantilever may be adopted as the stress testing part 19. Through precise design of cantilever structure, the cantilever can measure the stress signal accurately. The signals corresponding to the stress change arising from the change in the shape of cantilever can be converted into electrical signal and then output to the external testing equipment, thus a real-time monitoring of the stress signal could be realized.

After the sensor 11 is received in the sensor carrier 4, the sensor 11 will be tilted around X axis and Y axis along with the sensor carrier 4 and the sample holder body 2, while simultaneously, the stress will be applied on the sample 12, thus in-situ monitoring changes of mechanical and electrical signals through external signal input and output equipment can be realized.

In one embodiment, the electrodes are connected by conductive materials with exterior insulation.

In one embodiment, an insulating material covering a surface of the sample holder head 3, the sensor carrier 4, or the pressing piece 15 comprises silica, silicon carbon, silicon nitride, or hafnium oxide.

In one embodiment, the electrode array I 7, the electrode array II 14, or the electrode array III 16 is made of a material with good conductivity, the material is Rh, Pd, Rh/Au, Ti/Au, W/Pt, Cr/Pt, Ni/Pt, Ag, or Cu.

The present disclosure has a number of advantages as described below.

First, the present disclosure provides a double tilt sample holder for in-situ measuring mechanical and electrical properties of microstructures in the TEM. The in-situ measurement is realized by applying sophisticated machining and semiconductor processing techniques.

Second, through the sophisticated structural design, the sample holder can tilt at a relatively larger angle around both X- and Y-axes, thus high-resolution images could be obtained from the best zone axis of a crystal. As a result, a direct observation of corresponding mechanical mechanism and electrical mechanism of nanomaterials under the in-plane stress could be realized.

Third, the present disclosure is applicable not only to one-dimensional nanostructures such as nanowires, nanobelts and nanotubes, but also to two-dimensional thin-films as well as to bulk TEM sample, thus providing a powerful tool for in-situ study of deformation mechanism of materials at atomic scale.

Fourth, in the present disclosure, the electrical connection between the external testing equipment and the testing sample is via a pressing piece. Such design would greatly shorten the length of the electrical wires used to connect the TEM sample to the external testing equipment. As a result, the tilting of the sample holder around Y-axis would not be hindered by those connecting electrical wires. Thus through the sophisticated structural design, the present disclosure solves the common tilting problem caused by direct introducing the electrical connection to the sample in the current available TEM sample holders.

Finally, the present disclosure allows using different sensor configurations according to specific requirement to conduct in-situ testing at atomic scale.

BRIEF DESCRIPTION OF DRAWINGS

In FIGS. 1-7, various components are labeled as follows: 1—handle, 2—sample holder body, 3—sample holder head, 4—sensor carrier, 5—supporting shafts, 6—conductor wires I, 7—electrode array I, 8—electrode interface, 9—Y-axis tilting actuator, 10—groove, 11—sensor, 12—sample, 13—through hole I, 14—electrode array II, 15—pressing piece, 16—electrode array III, 17—through hole II, 18—stress loading part, 19—stress testing part, 20—testing electrodes

DETAILED DESCRIPTION OF SAMPLE EMBODIMENTS

A specific embodiment of the present disclosure will now be described below by referring to the accompanying drawings.

Figure 1:
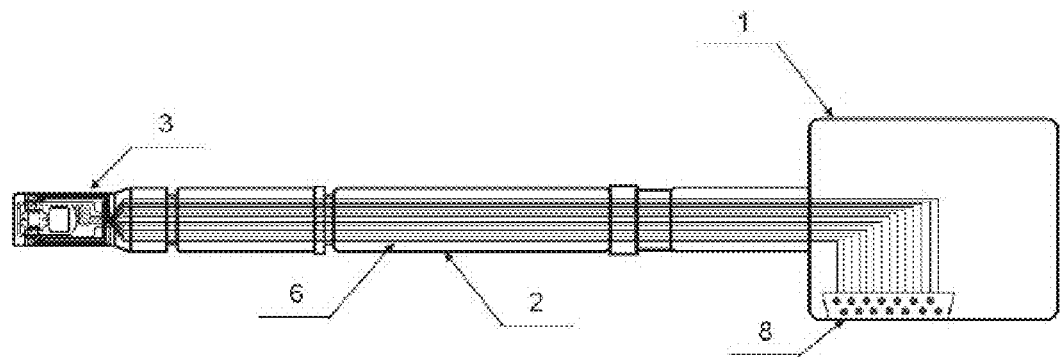
FIG. 1 is a side view of a double tilt transmission electron microscope (TEM) sample holder in accordance with the present disclosure.
Figure 2:
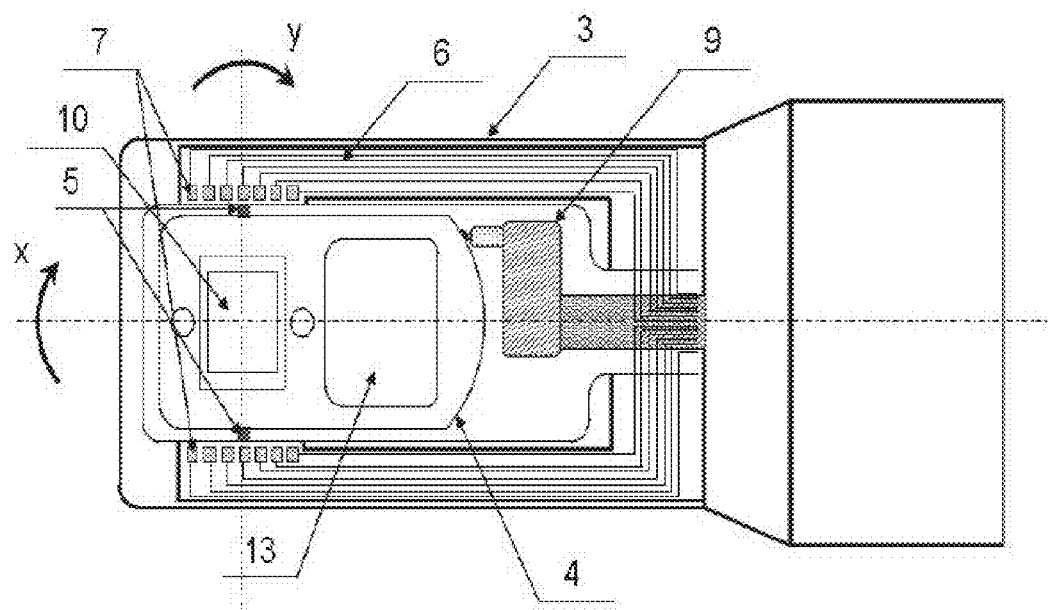
FIG. 2 is an enlarged view of a sample holder head in accordance with the present disclosure.
Figure 3:
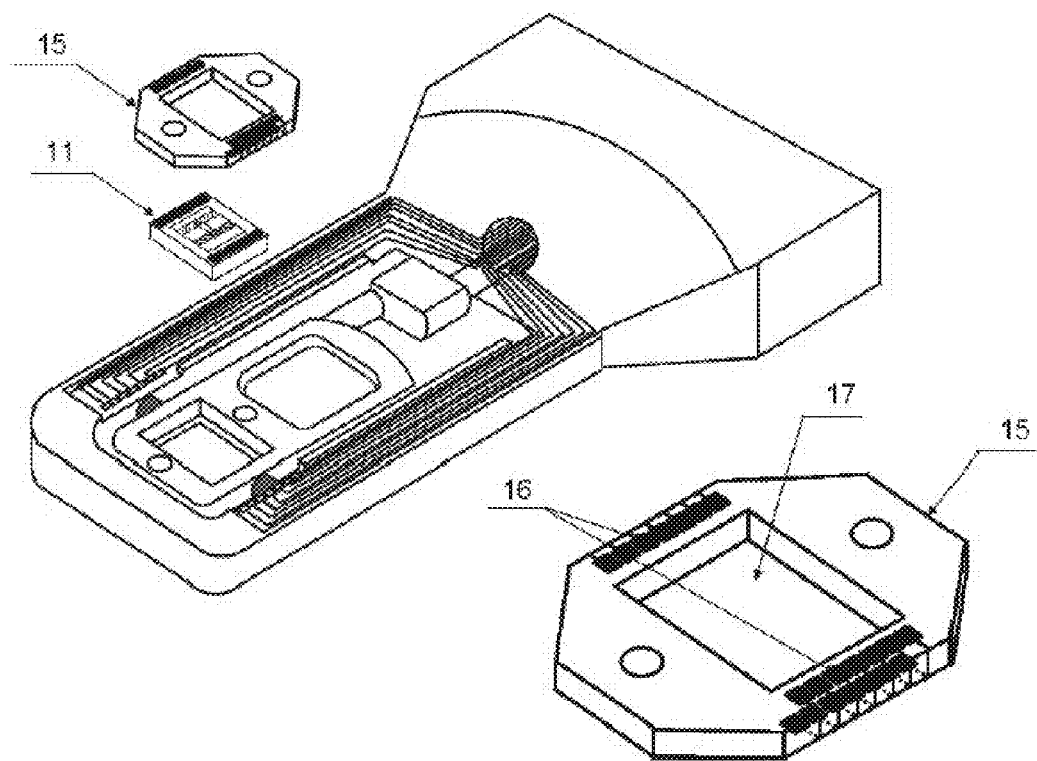
FIG. 3 is a perspective view of the sample holder head assembly in accordance with the present disclosure.
Figure 4:
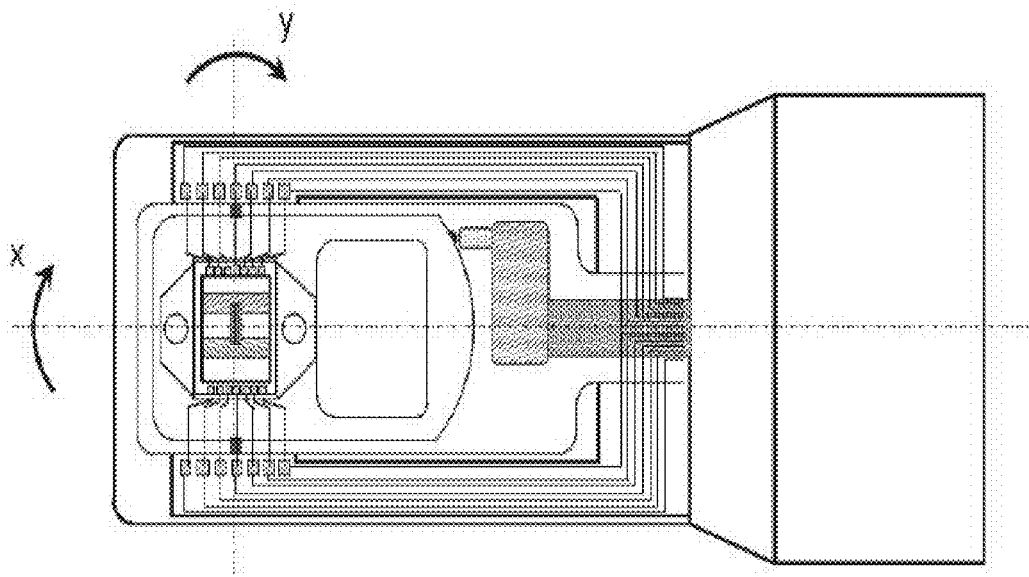
FIG. 4 is a top view of an assembled sample holder head in accordance with the present disclosure.
Figure 5:
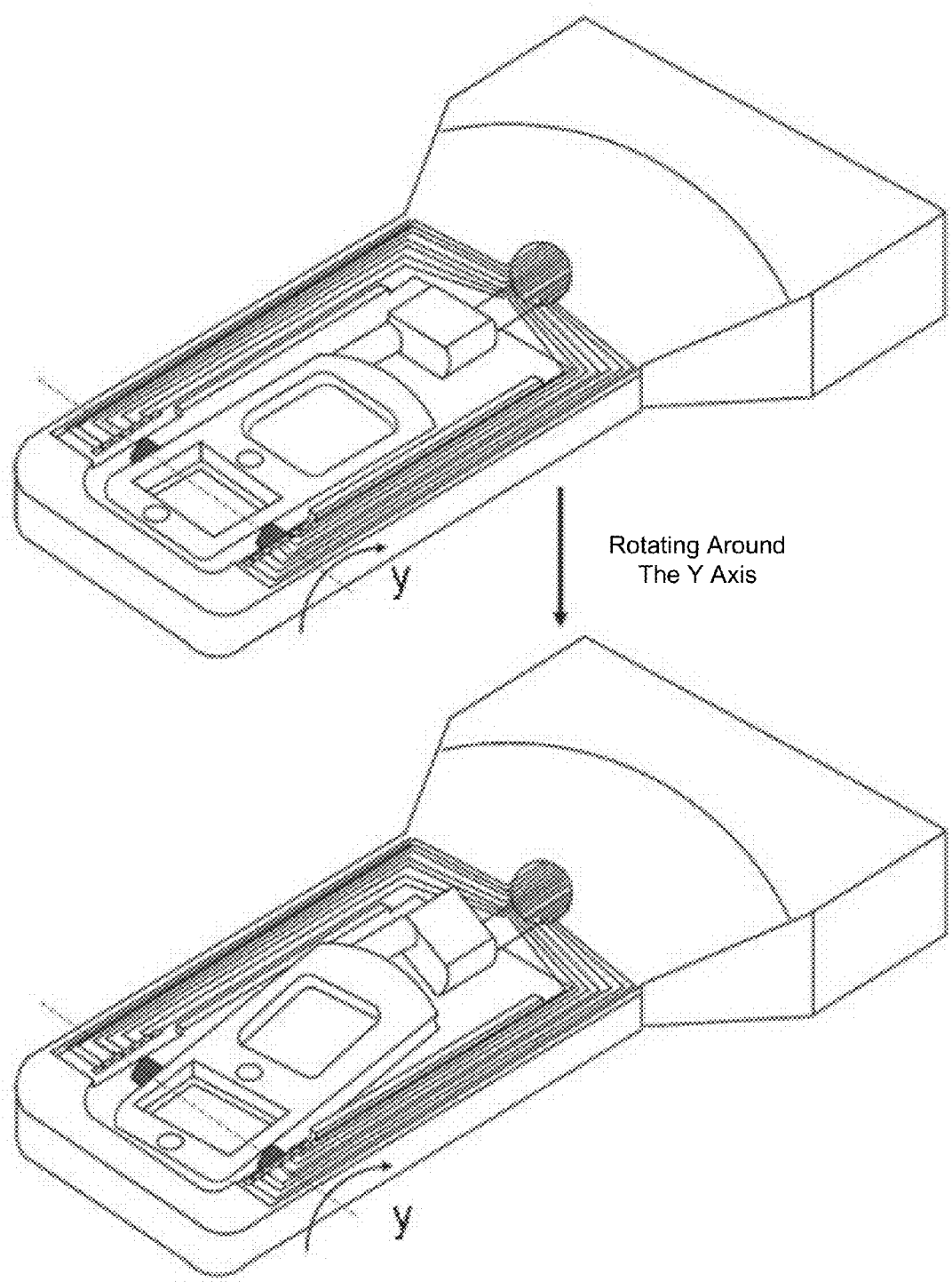
FIG. 5 is a perspective view of a sample holder head showing rotation around Y axis in accordance with the present disclosure.
Figure 6:
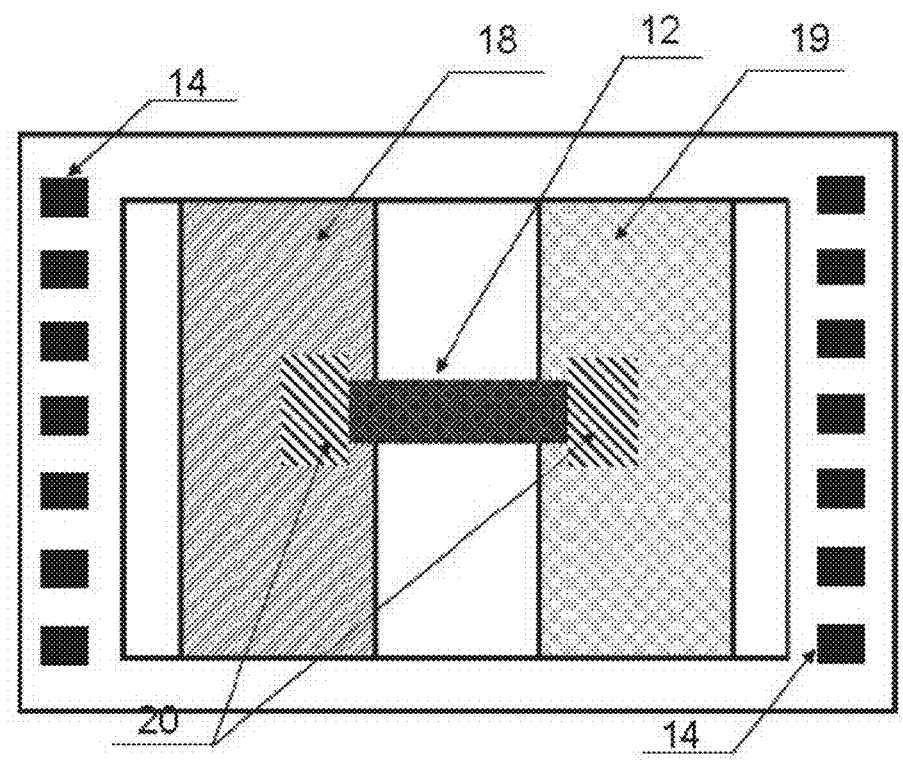
FIG. 6 is a top view of a sensor in accordance with the present disclosure.

As shown in FIGS. 1-6, a double tilt sample holder for in-situ measuring mechanical and electrical properties in a transmission electron microscope (TEM) generally may include a handle 1, a sample holder body 2, a sample holder head 3, a sensor carrier 4, and a pressing piece 15. The sensor carrier 4 is fixed on the front end of the sample holder head 3 by a pair of supporting shafts 5 located on the sides of the sample holder head 3. The sensor carrier can tilt within the plane perpendicular to the sample holder head 3 by rotating around the supporting shafts 5 (i.e. tilting around Y axis at an angle of ±30°). The conductor wires I 6 led into the sample holder head 3 through sample holder body 2 from the outside of the TEM are distributed in a symmetrical manner along sides of the sample holder head 3. One end of the conductor wires 6 is connected to the electrode array I 7 distributed along the sides of the sample holder head 3, and the other end of the conductor wires I 6 is connected to the electrode interface 8. The electrode interface 8 is connected to the external equipment of the TEM. The electrode array I 7 is symmetrically distributed along the sides of the sample holder head 3 with the supporting shafts 5 as the centerline. The rotation of the sensor carrier 4 is driven by a Y-axis tilting actuator 9 located at its end. The sensor carrier 4 may include a groove 10 located at a position with the supporting shafts 5 as the centerline. The groove 10 is a through hole with a peripheral supporting edge at the bottom to support a sensor 11. The electrode array I 7 is symmetrically distributed at two side walls of the sample holder head 3 with the supporting shafts 5 as the centerline. The sensor carrier 4 is driven by the Y-axis tilting actuator 9 located at its end for rotation. The sensor carrier 4 may include a groove 10 located at a position with the supporting shafts 5 as the centerline. The groove 10 is a through hole with a peripheral supporting edge at the bottom to support a sensor 11. In addition, the sensor carrier 4 may also have a through hole I 13 located at a position far from the supporting shafts 5 and close to the Y-axis tilting actuator 9. The dimension of the through hole I 13 is configured in such a way that the sensor carrier 4 will not be in contact with the pole shoe of the TEM when the sample holder tilts around the Y axis and when the sample holder fully revolves around X axis, thus preventing damages to the TEM. Commercially available sensors can be used in the present disclosure. The stress loading part 18 is a bimetal strip equipped with a heating resistance and a thermocouple element. The commercially available cantilever may be adopted as the stress testing part 19. The stress testing part 19 is a silicon (Si) cantilever beam having a Wheatstone bridge system for measuring the deflection displacement. The displacement will be converted to corresponding stress signal through external testing equipment. The assemble of the sample holder head is shown in FIG. 3, first, the sample 12 is fixed on testing electrodes of 20, then the sensor 11 is received in the groove 10 of the sensor carrier 4 and secured on the sensor carrier 4 by the pressing piece 15. Each electrode of the electrode array III 16 on the lower surface of the pressing piece is connected to the respective one of the electrode array II 14 on the sensor 11. The thickness of the sensor 11 and the depth of groove 10 are configured such that they are in the same plane as the focusing point of the TEM electron beam once the sensor 11 is received in the groove 10, thus the TEM electron beam can focus on the sample 12 and then pass through the gap on the sensor 11 and the through hole I 13. Each electrode of the electrode array III 16 on the upper surface of the pressing piece 15 is connected to the respective one of the electrode array I 7 on the sample holder head 3 through a conductor wire. The electron beam is focused on sample 12 via the through hole II 17 provided on the pressing piece 15. The assembled sample holder as illustrated in FIG. 5 is first put into the TEM, and then the assembled sample holder is connected to the external testing equipment through electrode interface 8. The electron beam of the TEM is then turned on and the testing sample is found under the viewfinder. If the sample is a single crystal sample, the sample is tilted below the low-index positive band axis. When testing, the driving signal is given to the stress loading part 18 through the external equipment, thus applying force on the sample 12. The response detected by the stress testing part 19 is then transferred to the external testing equipment to obtain stress-strain relationship. Simultaneously, the voltage will be applied on the sample through the testing electrodes 20, and then the mechanical and electrical correspondence will be observed under the TEM.

Figure 7:
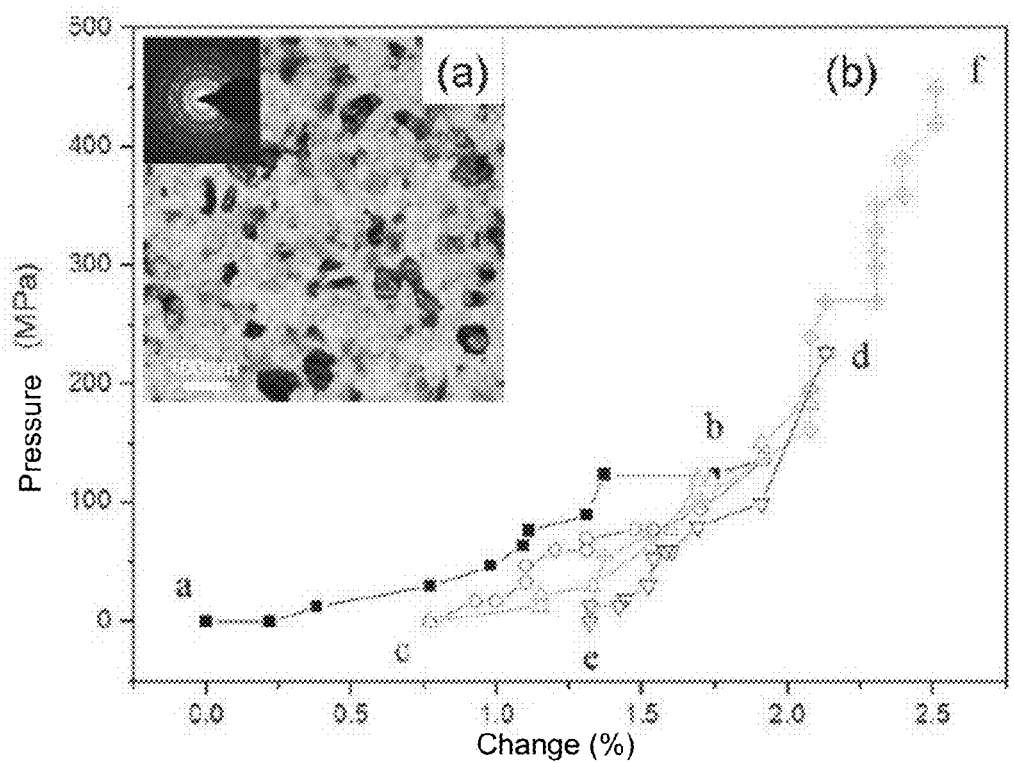
FIG. 7 is a TEM image of a polycrystalline Al film and stress-strain curves.

FIG. 7a is a TEM image of a polycrystalline Al film sample and inset shows the selected area diffraction pattern of the polycrystalline Al film. FIG. 7b shows the stress-strain curves of the polycrystalline Al film sample obtained by using the sample holder of the present disclosure during tensile deformation.

The sensor 11 can also use sensors disclosed in Chinese Patent No. ZL200610144031.X, entitled A TEM GRID DRIVEN BY A THERMAL BIMETAL STRIP; Chinese Patent No. ZL200810056836.8, entitled STRESS TEST GRID OF NANOMATERIALS FOR TEM USE; and Chinese Patent Application No. 200920269907.2, entitled SENSOR FOR QUANTITATIVE TEST ON ELECTROMECHANICAL PERFORMANCE AND MICROSCOPIC STRUCTURE AND FABRICATIO METHOD.

What is claimed is:

1. A double tilt sample holder for in-situ measuring mechanical and electrical properties in a transmission electron microscope (TEM), comprising:
   a handle having an electrode interface connecting to external equipment of the TEM;
   a sample holder body having conductor wires connecting to the electrode interface;
   a sample holder head located at a front end of the sample holder, comprising:

a pair of supporting shafts located on sides of the sample holder head, a first electrode array having two rows of electrodes symmetrically disposed along sides of the sample holder head with the supporting shafts as the centerline and connecting to the conductor wires, a Y-axis tilting actuator, and a sensor carrier fixed on the front end of the sample holder head by the supporting shafts, the sensor carrier comprising:
- a through groove having a peripheral supporting edge at a bottom of the through groove with the supporting shafts as the centerline, and
- a first through hole located at a position away from the supporting shafts and closer to the Y-axis tilting actuator;

a sensor, comprising:
- a second electrode array having two rows of electrodes disposed along sides of the sensor,
- a stress loading part disposed between and in parallel to rows of the second electrode array,
- a stress testing part disposed between and in parallel to rows of the second electrode array, and
- two testing electrodes configured to hold a sample,
- wherein a first testing electrode is disposed on the stress loading part and a second testing electrode is disposed on the stress testing part,
- wherein a small gap formed between the stress loading part and stress testing part is configured to pass an electron beam of the TEM through,
- wherein the stress loading part, the stress testing part, and the first and second testing electrodes are electrically connected to corresponding electrode of the second electrode array,
- wherein a material of the stress loading part can undergo deformation under external thermal or electric field and is a bimetal strip, a piezoelectric ceramic, or a memory alloy, and
- wherein the stress testing part applies the cantilever technology structure; and a pressing piece comprising:
- a second through hole, configured to allow the TEM electron beam passing through the pressing piece and focusing on the sample, and
- a third electrode array having two rows of electrodes on both an upper surface and a lower surface of the pressing piece, the third electrode array is configured such that each electrode on the upper surface of the pressing piece is correspondingly aligned with a respective one of the first electrode array, each electrode on the lower surface of the pressing piece is correspondingly aligned with a respective one of the second electrode array, and each electrode of the third electrode array on the upper surface of the pressing piece is electrically connected to a respective one on the lower surface of the pressing piece;

wherein the dimension of the through groove is configured such that after the sensor is received in the through groove, a upper surface plane of the sensor and a focusing point of the TEM electron beam are in the same plane; and wherein the sensor carrier is driven by the Y-axis tilting actuator to tilt around Y-axis.

2. The sample holder as recited in claim 1, wherein the electrodes are connected by conductive materials with exterior insulation.

3. The sample holder as recited claim 1, wherein an insulating material covering a surface of the sample holder head, the sensor carrier, or the pressing piece comprises silica, silicon carbon, silicon nitride, or hafnium oxide.

4. The sample holder as recited claim 1, wherein the first electrode array, the second electrode array, or the third electrode array is made of a material with good conductivity, the material is Rh, Pd, Rh/Au, Ti/Au, W/Pt, Cr/Pt, Ni/Pt, Ag, or Cu.

* * * * *